US008626264B1

(12) United States Patent
Beran

(10) Patent No.: US 8,626,264 B1
(45) Date of Patent: Jan. 7, 2014

(54) OBTAINING INFORMATION ABOUT BRAIN ACTIVITY

(76) Inventor: James T. Beran, Richmond, VA (US)

( * ) Notice: Subject to any disclaimer, the term of this patent is extended or adjusted under 35 U.S.C. 154(b) by 709 days.

(21) Appl. No.: 12/384,730

(22) Filed: Apr. 8, 2009

Related U.S. Application Data

(60) Provisional application No. 61/123,504, filed on Apr. 9, 2008.

(51) Int. Cl.
*A61B 5/00* (2006.01)

(52) U.S. Cl.
USPC .......... 600/407; 600/410; 600/436; 600/544

(58) Field of Classification Search
USPC ......... 600/300, 407, 410, 411, 436, 544, 545; 324/300, 309
See application file for complete search history.

(56) References Cited

U.S. PATENT DOCUMENTS

| | | | | |
|---|---|---|---|---|
| 4,907,597 | A | * | 3/1990 | Chamoun ............... 600/544 |
| 5,010,891 | A | * | 4/1991 | Chamoun ............... 600/544 |
| 5,320,109 | A | * | 6/1994 | Chamoun et al. ........ 600/544 |
| 5,372,137 | A | | 12/1994 | Wong et al. |
| 5,458,117 | A | * | 10/1995 | Chamoun et al. ........ 600/547 |
| 5,495,853 | A | | 3/1996 | Yasushi |
| 5,603,322 | A | | 2/1997 | Jesmanowicz et al. |
| 5,632,276 | A | | 5/1997 | Eidelberg et al. |
| 5,662,112 | A | | 9/1997 | Heid |
| 6,018,675 | A | | 1/2000 | Apkarian et al. |
| 6,073,041 | A | | 6/2000 | Hu et al. |
| 6,289,234 | B1 | | 9/2001 | Mueller |
| 6,298,258 | B1 | | 10/2001 | Heid et al. |
| 6,370,416 | B1 | | 4/2002 | Rosenfeld |
| 6,377,833 | B1 | | 4/2002 | Albert |
| 6,470,202 | B2 | | 10/2002 | Rosenfeld |
| 6,490,472 | B1 | | 12/2002 | Li et al. |
| 6,528,997 | B2 | | 3/2003 | Zhong et al. |
| 6,622,036 | B1 | * | 9/2003 | Suffin ................... 600/544 |
| 6,759,848 | B2 | | 7/2004 | Kruger |
| 6,768,915 | B2 | | 7/2004 | Brand et al. |
| 6,907,280 | B2 | | 6/2005 | Becerra et al. |
| 6,917,199 | B2 | | 7/2005 | Jara |
| 7,069,067 | B2 | | 6/2006 | Kuth |
| 7,171,339 | B2 | | 1/2007 | Repucci et al. |
| 7,177,675 | B2 | * | 2/2007 | Suffin et al. ............ 600/544 |
| 7,187,790 | B2 | | 3/2007 | Sabol et al. |

(Continued)

OTHER PUBLICATIONS

Wagner, A.D., "Early detection of Alzheimer's disease: An fMRI marker for people at risk?", Nature Neuroscience, vol. 3, No. 11, Oct. 2000, pp. 973-974.

(Continued)

*Primary Examiner* — Unsu Jung
*Assistant Examiner* — Phong K Huynh

(57) ABSTRACT

A brain imaging system can be operated to obtain brain image signals indicating activity at brain locations, and information can be extracted from the brain image signals. For example, for each of a set of living human brain regions that can have two or more possible activity features such as qualia features, feature values can be obtained indicating activity features of the region. The feature values can be more explicit than brain image data indicating activity at brain locations. A data structure can be produced that includes data indicating extracted information, such as qualia value data for a quale activity feature that can occur in a region. Such a data structure can be stored on a storage medium and used in diagnosis and/or treatment of detrimental conditions of consciousness.

14 Claims, 7 Drawing Sheets

(56) References Cited

U.S. PATENT DOCUMENTS

| | | | |
|---|---|---|---|
| 7,565,193 B2 | 7/2009 | Laken | |
| 7,627,370 B2 | 12/2009 | Marks | |
| 7,729,755 B2 | 6/2010 | Laken | |
| 7,899,524 B2 | 3/2011 | Kozel | |
| 7,917,190 B2 | 3/2011 | Mistretta et al. | |
| 8,014,847 B2 | 9/2011 | Shastri et al. | |
| 8,029,431 B2 * | 10/2011 | Tononi | 600/9 |
| 8,457,731 B2 * | 6/2013 | Tonini | 600/544 |
| 2002/0042563 A1 * | 4/2002 | Becerra et al. | 600/411 |
| 2004/0120557 A1 * | 6/2004 | Sabol et al. | 382/128 |
| 2005/0119547 A1 | 6/2005 | Shastri et al. | |
| 2006/0036152 A1 | 2/2006 | Kozel | |
| 2006/0036153 A1 | 2/2006 | Laken | |
| 2006/0084858 A1 | 4/2006 | Marks | |
| 2007/0112585 A1 | 5/2007 | Breiter et al. | |
| 2007/0167728 A1 | 7/2007 | Mistretta et al. | |
| 2009/0036799 A1 | 2/2009 | Sandhu et al. | |
| 2009/0221930 A1 | 9/2009 | Laken | |

OTHER PUBLICATIONS

Zimmer, C., "Neuron Network Goes Awry, and Brain Becomes an IPod", New York Times, Jul. 12, 2005, pp. D1, D6.
"What's so funny?", Richmond Times-Dispatch, Jul. 28, 2005.
Blakeslee, S., "Discovering That Denial of Paralysis Is Not Just a Problem of the Mind", New York Times, Aug. 2, 2005, p. D3.
Wingert, P. and Brant, M., "Reading your Baby's Mind", Newsweek, Aug. 15, 2005, pp. 32-39.
McNeil, D.G., Jr., "This Is Your Brain on Chocolate", New York Times, Aug. 23, 2005, p. D1.
Blakeslee, S., "This Is Your Brain Under Hypnosis", New York Times, Nov. 22, 2005, pp. D1, D4.
Carey, B., "Holding Loved One's Hand Can Calm Jittery Neurons", New York Times, Jan. 31, 2006, p. D7.
Carey, B., "Searching for the Person in the Brain", New York Times, Section 4, pp. 1, 4.
Kinetz, E., "Is Hysteria Real? Brain Images Say Yes", New York Times, Sep. 26, 2006, pp. D1, D4.
Goodman, B., "Certain Areas of the Brain Size Up Your Competition", New York Times, Oct. 31, 2006, p. D8.
Fleck, C., "Mindreading: What goes on in your head may no longer be a secret", AARP Bulletin, Nov. 2006, p. 24.
Blakeslee, S., "A Small Part of the Brain, and Its Profound Effects", New York Times, Feb. 6, 2007, p. D6.
"Brain uses regions to maintain its focus", Richmond Times-Dispatch, Mar. 30, 2007, p. A4.
Kayser, C., "Listening with your Eyes", Scientific American Mind, Apr./May 2007, pp. 24-29.
Shrock, K., "Freeing a Locked-In Mind", Scientific American Mind, Apr./May 2007, pp. 40-45.
Miller, S.E., "The Brain: A Legal Pandora's Box", IP Law and Business, May 2007, pp. 25-26.
Dickerson, B.C., "Advances in Functional Magnetic Resonance Imaging: Technology and Clinical Applications", Neurotherapeutics, vol. 4, Issue 3, Jul. 2007, pp. 360-370.
Tsien, J.Z., "The Memory Code", Scientific American, Jul. 2007, pp. 52-59.
Blakeslee, S. and Blakeslee, M., "Where Mind and Body Meet", Scientific American Mind, Aug./Sep. 2007, pp. 44-51.
Biello, D., "Searching for God in the Brain", Scientific American Mind, Oct./Nov. 2007, pp. 38-45.
Hutson, M., "Neurorealism", New York Times Magazine, Dec. 9, 2007, pp. 84, 86.
Curtis, D., "Bridging the worlds of neuroscience and the law", California Bar Journal, Mar. 2008, pp. 1, 7.
Carpenter, S., "Buried Prejudice", Scientific American Mind, Apr./May 2008, pp. 32-39.
Portner, M., "The Orgasmic Mind", Scientific American Mind, Apr./May 2008, pp. 66-71.
Intagliata, C., "Can You Read My Mind?", Scientific American Mind, Jun./Jul. 2008, p. 11.
Gieler, U. and Walter, B., "Scratch This!", Scientific American Mind, Jun./Jul. 2008, pp. 52-59.
Gura, T., "Addicted to Starvation", Scientific American Mind, Jun./Jul. 2008, pp. 60-67.
Haler, R.J., "What are ideas?", Scientific American Mind, Jun./Jul. 2008, p. 84.
Hurley, D., "The Science of Sarcasm (Not That You Care)", New York Times, Jun. 3, 2008, p. D6.
Carey, B., "Scientists Identify the Brain's Activity Hub", New York Times, Jul. 1, 2008, p. D6.
"Infant's Smile Works on Mom's Brain", New York Times, Jul. 22, 2008, p. D6.
Carey, B., "For the Brain, Remembering Is Like Reliving", New York Times, Sep. 5, 2008, pp. A1, A22.
Swaminathan, N., "Brain-Scan Mystery Solved", Scientific American Mind, Oct./Nov. 2008, p. 7.
Shermer, M., "Why You Should Be Skeptical of Brain Scans", Scientific American Mind, Oct./Nov. 2008, pp. 66-71.
Koch, C., "Measure More, Argue Less", Scientific American Mind, Feb./Mar. 2009, pp. 16-17.
Kamitani, Y. and Tong, F., "Decoding the visual and subjective contents of the human brain", Nature Neuroscience, vol. 8, No. 5, May 2005, pp. 679-685.
Knierim, J.J., "The Matrix in Your Head", Scientific American Mind, Jun./Jul. 2007, pp. 42-49.
Beran, J., "Disambiguation in Conscious Cavities", in Quantum Mind 2007, Salzburg, Austria, Jul. 2007, Conference Abstracts, p. 30.
Soon, C.S., et al., Unconscious determinants of free decisions in the human brain, Nature Neuroscience, vol. 11, No. 5, May 2008, pp. 543-545.
Hafting, T., Fyhn, M., Molden, S., Moser, M.-B., and Moser, E.I., "Microstructure of a spatial map in the entorhinal cortex", Nature, vol. 436, Aug. 11, 2005, pp. 801-806.
Sargolini, F., et al., "Conjunctive Representation of Position, Direction, and Velocity in Entorhinal Cortex", Science, vol. 312, May 5, 2006, pp. 758-762.
Kontos, D., et al., Identifying Discriminative fMRI Activation Signatures in Alzheimer's Disease: Studying a Series of Semantic Decision Tasks, Human Brain Mapping Conference (OHBM Budapest, Hungary, Jun. 13-17, 2004, 3 pages.
Hwang, D.Y., and Golby, A.J., "The brain basis for episodic memory: Insights from functional MRI, intracranial EEG, and patients with epilepsy", Epilepsy and Behavior, vol. 8, 2006, pp. 115-126.
Friston, K., "Chapter 1: A short history of SPM", Friston, K., et al., Eds., Statistical Parametric Mapping, London: Academic/Elsevier, 2007, pp. 3-9.
Friston, K., "Chapter 2: Statistical parametric mapping", Friston, K., et al., Eds., Statistical Parametric Mapping, London: Academic/Elsevier, 2007, pp. 10-31 and Pl. 1-2.
Friston, K. et al., "Chapter 3: Modelling brain responses", Friston, K., et al., Eds., Statistical Parametric Mapping, London: Academic/Elsevier, 2007, pp. 32-45 and Pl. 3.
Penny, W. et al.,"Chapter 25:Spatio-temporal models for fMRI", Friston, K., et al.,Eds., Statistical Parametric Mapping,London:Academic/Elsevier, 2007, pp. 313-322, Pl. 23-25.
Penny, W. et al.,"Chapter 26:Spatio-temporal models for EEG",Friston, K., et al.,Eds., Statistical Parametric Mapping, London:Academic/Elsevier, 2007, pp. 323-336, Pl. 26-36.
Kilner, J., et al., "Chapter 32: Neuronal models of energetics", Friston, K., et al., Eds., Statistical Parametric Mapping, London: Academic/Elsevier, 2007, pp. 406-413.
Friston, K., and Buchel, C., "Chapter 37: Functional connectivfity: eigenimages and multivariate analyses", Friston K.. et al., Eds., Statistical Parametric Mapping, London: Academic/Elsevier, 2007, pp. 492-507 and Pl. 53-54.
Harrison, L. et al.,"Chapter 38: Effective connectivity", Friston, K., et al., Eds., Statistical Parametric Mapping, London:Academic/Elsevier, 2007, pp. 508-521 and Pl. 55-56.
Penny, W., and Harrison, L., "Chapter 40: Multivariate autoregressive models", Friston, K., et al., Eds., Statistical Parametric Mapping, London: Academic/Elsevier, 2007, pp. 534-540 and Pl. 57.

(56) References Cited

OTHER PUBLICATIONS

Friston, K., "Chapter 41: Dynamic Causal Models for fMRI", Friston, K., et al., Eds., Statistical Parametric Mapping, London: Academic/Elsevier, 2007, pp. 541-560 and Pl. 58.

Friston, K., Kiebel, S., Garrido, M., and David, O., "Chapter 42: Dynamic Causal Models for EEG", Friston, K.. et al., Eds., Statistical Parametric Mapping, London: Academic/Elsevier, 2007, pp. 561-576 and Pl. 59-60.

Stephan, K.E., and Penny, W. D., "Chapter 43: Dynamic Causal Models and Bayesian selection", Friston, K., et al., Eds., Statistical Parametric Mapping, London: Academic/Elsevier, 2007, pp. 577-585 and Pl. 61.

Del Cul, A., Baillet, S., and Dehaene, S., "Brain Dynamics Underlying the Nonlinear Threshold for Access to Consciousness", PLoS Biology, vol. 5, Issue 10, Oct. 2007, pp. 2408-2423.

Blakeslee, S., and Blakeslee, M., The Body Has a Mind of Its Own, New York: Random House, 2007, pp. 54-70, 86, 174-188, and 203-208.

Orrison, W.W., Jr., Lewine, J.D., Sanders, J.A., and Hartshorne, M.F., Functional Brain Imaging, St. Louis: Mosby, 1995, pp. 1-12, 90-94 97-142, 164-185, 190-207, 213-215, 222-233, 306-319, 340-367, 381-382, 388-415, and 435-454.

Haynes, J.-D., and Rees, G., "Decoding Mental States from Brain Activity in Humans", Nature Reviews Neuroscience, vol. 7, No. 7, Jul. 2008, pp. 523-534.

Kay, K.N., Naselaris, T., Prenger, R.J., and Gallant, J.L., "Identifying Natural Images from Human Brain Activity", Nature, vol. 452, Mar. 20, 2008, pp. 352-358.

Bor, D., "The Mechanics of mind Reading", Scientific American Mind, Jul./Aug. 2010, pp. 52-57.

Michel, C.M., Koenig, T., and Brandeis, D., "Chapter 6: Electrical neuroimaging in the time domain", in Michel. C.M., et al., Eds., Electrical Neuroimaging, Cambridge, UK: Cambridge University Press, 2009, pp. 111-143.

Brandeis, D., Michel, C.M., Koenig, T., and Gianotti, L.R.R., "Chapter 10: Integration of electrical neuroimaging with other functional imaging methods", in Michel, C.M., et al., Eds., Electrical Neuroimaging, Cambridge, UK: Cambridge University Press, 2009, pp. 215-252.

Laureys, S., Boly, M., and Tononi, G., "Chapter 3: Functional Neuroimaging", in Laureys, S., et al., The Neurology of Consciousness: Cognitive Neuroscience and Neuropathology, London, UK: Academic Press/Elsevier, 2009, pp. 31-42.

Kubler, A., "Chapter 17: Brain-Computer Interfaces for Communication in Paralysed Patients and Implications for Disorders of Consciousness", in Laureys, S., et al., The Neurology of Consciousness: Cognitive Neuroscience and Neuropathology, London, UK: Academic Press/Elsevier, 2009, pp. 217-233.

Kamitani, Y., and Tong, G., "Decoding Seen and Attended Motion Directions from Activity in the Human Visual Cortex", Current Biology, vol. 16, Jun. 6, 2006, pp. 1096-1102.

Beran, J., "Explanation of Jim Beran's Slides from Quantum Mind 2007", Aug. 18, 2007, printed from consciouscavity.com, 26 pages.

Beran, J., "Image-based Information About Consciousness: Choosing Models for Effective Diagnosis and Therapy", Toward a Science of Consciousness, Apr. 8-12, 2008, pp. 175-176.

Langleben, D., "fMRI Studies of Deception", Toward a Science of Consciousness, Apr. 8-12, 2008, p. 88.

Owen, A., "Using fMRI to Detect Consciousness in the Absence of Behavioral Signs", Toward a Science of Consciousness, Apr. 8-12, 2008, pp. 88-89.

Tong, F., "Decoding Visual Perception: From Brain Reading to Mind Reading", Toward a Science of Consciousness, Apr. 8-12, 2008, pp. 100-101.

Beran, J., "The Road to Reading Qualia", Apr. 9, 2008, 2 pages.

Beran, J., "Jim Beran's Poster Presentation at Tucson 2008", Apr. 25, 2008, printed from consciouscavity.com, 10 pages.

Boynton, G.M., "Imaging orientation selectivity: decoding conscious perception in V1", Nature Neuroscience, vol. 8, No. 5, May 2005, pp. 541-542.

Haynes, J.-D. and Rees, G., "Predicting the orientation of invisible stimuli from activity in human primary visual cortex", Nature Neuroscience, vol. 8, No. 5, May 2005, pp. 686-691.

Haynes, J.-D. and Rees, G., "Predicting the Stream of Consciousness from Activity in Human Visual Cortex", Current Biology, vol. 15, Jul. 26, 2005, pp. 1301-1307.

Haynes, J.-D. and Rees, G., "Decoding mental states from brain activity in humans", Nature Reviews Neuroscience, vol. 7, No. 7, Jul. 2006, pp. 523-534.

Miyawaki, Y. et al., "Visual Image Reconstruction from Human Brain Activity using a Combination of Multiscale Local Image Decoders", Neuron, vol. 60, Dec. 11, 2008, pp. 915-929.

Seymour, K. et al., "The Coding of Color, Motion, and Their Conjunction in the Human Visual Cortex", Current Biology, vol. 19, Feb. 10, 2009, pp. 177-183.

Kay, K.N. and Gallant, J.L., "I can see what you see", Nature Neuroscience, vol. 12, No. 3, Mar. 2009, pp. 245-246.

Owen, A.M. et al., "Detecting Awareness in the Vegetative State", Science, vol. 313, Sep. 8, 2006, p. 1402.

\* cited by examiner

US 8,626,264 B1

OBTAINING INFORMATION ABOUT BRAIN ACTIVITY

This application claims the benefit of U.S. Provisional Patent Application No. 61/123,504, filed Apr. 9, 2008, entitled "Obtaining Information About Brain Activity", which is incorporated herein by reference in its entirety.

This application describes techniques that obtain information about brain activity. More specifically, information can be obtained from signals that result from brain imaging.

Various techniques have been proposed for brain imaging and for obtaining information from brain image signals. Some have even proposed that brain imaging techniques could be used to perform "mind reading".

It would be advantageous to have improved techniques that obtain information from brain image signals.

SUMMARY

The invention provides several embodiments, including methods, articles, and systems. In general, each embodiment involves values for activity features of brain regions.

These and other features and advantages will be understood from the figures and description.

DETAILED DESCRIPTION

Figure 1:
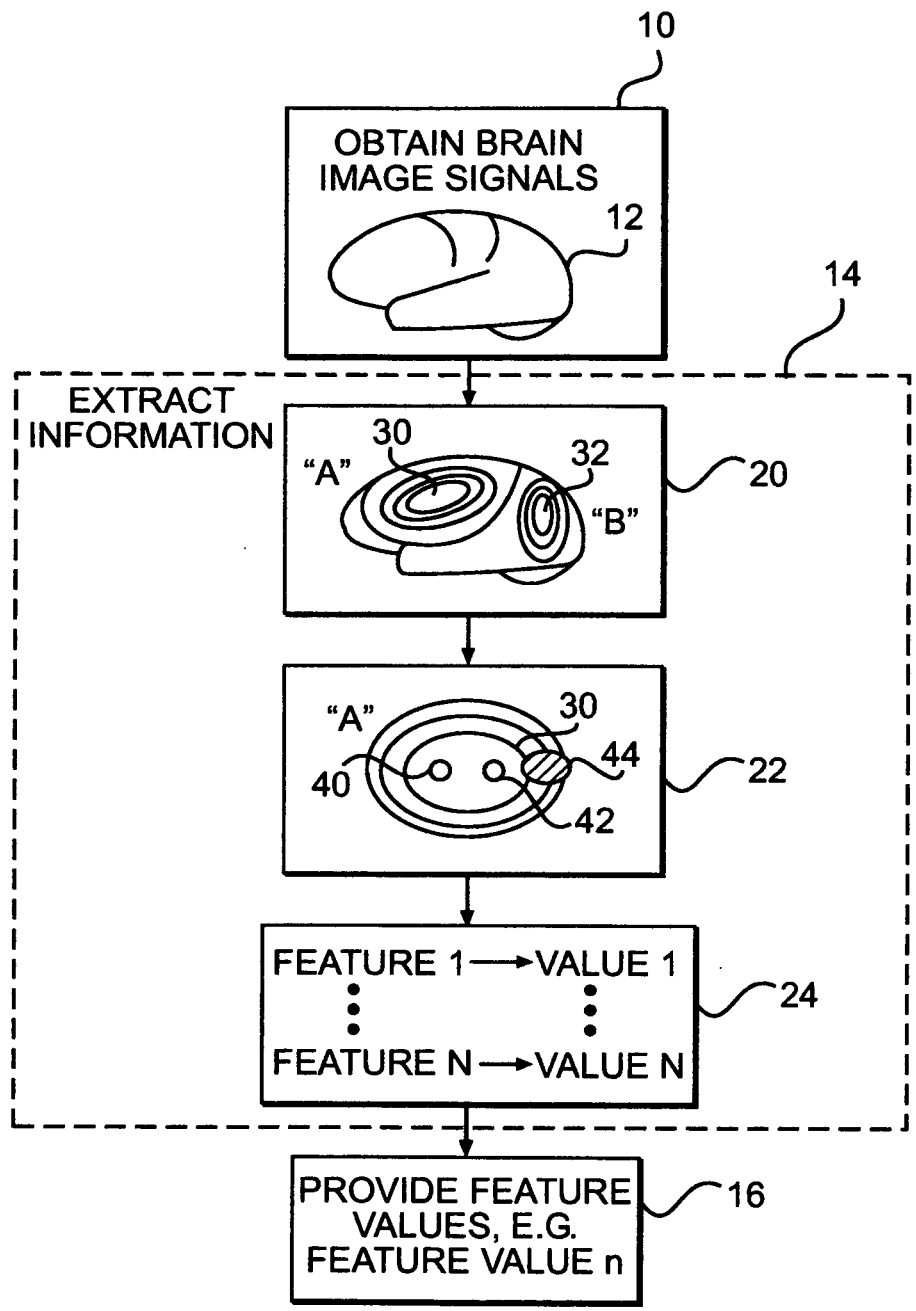
FIG. 1 is a schematic flow diagram showing generally how brain image signals could be used to provide feature values for activity features of an active brain region.

In the following detailed description, numeric values and ranges are provided for various aspects of the implementations described. These values and ranges are to be treated as examples only, and are not intended to limit the scope of the claims.

Implementations described below involve signal processing and brain imaging. As used herein, the term "signal" includes any physical phenomenon that can carry information through space and/or time, whether the information is carried in analog, digital, or other form. The term "electrical/magnetic signal" is used herein to encompass all types of signals that can transfer, store, or otherwise carry information through electricity, magnetism, and or electromagnetism; electrical/magnetic signals thus include but are not limited to voltage- and current-based electrical signals, propagating electromagnetic signals including light in any range of photon energies, flux- or orientation-based magnetic signals, capacitively stored charge, magnetic domain orientations, optically readable and/or recordable features of storage media, states of an electronic bistable or multistable device such as a flip-flop, and signals of various others kinds in which information can be transferred and/or stored.

As used herein, the term "brain image signals" refers to signals that include information about a brain that can be mapped into an image. As described in Orrison, W. W., Jr., Lewine, J. D., Sanders, J. A., and Hartshorne, M. F., Functional Brain Imaging, St. Louis: Mosby, 1995, incorporated herein by reference, several techniques have been developed for obtaining electrical/magnetic brain image signals, including tomographic techniques such as positron emission tomography (PET); magnetic resonance techniques such as functional magnetic resonance imaging (fMRI); techniques based on electrical potential sensing such as electroencephalography (EEG); techniques based on sensing magnetic signals from a brain such as magnetoencephalography (MEG); and combinations of two or more such techniques, such as fMRI and MEG.

Implementations described below involve operations that extract information from brain image signals. As used herein, an operation "extracts" information from signals if it uses the signals to obtain other signals in which the information is more explicitly indicated. For example, raw, unprocessed analog brain image signals from one of the techniques described above can implicitly indicate differences between brain regions; the raw signals can be used to obtain position value data that indicate respective values for positions in the brain regions, and that therefore indicate differences between brain regions less implicitly, i.e. more explicitly, than the raw signals; the position value data can in turn be used to present a visual signal such as an image in which a human can more explicitly see differences between regions. Increasing explicitness can be shown by ease of human perception, but other indices of increasing explicitness include, for example, greater conciseness and a greater ratio of relevant to non-relevant information, such as signal-to-noise ratio.

Difficulties arise in extracting information from brain image signals. For example, brain imaging techniques like those described above can produce huge amounts of information about a brain, and the volume of data can make it difficult to extract desired information; techniques described by Friston, K. J., Ashburner, J. T., Kiebel, S. J., Nichols, T. E., and Penny, W. D., Eds., *Statistical Parametric Mapping—The Analysis of Functional Brain Images*, London: Academic Press, 2007, for example, illustrate the exquisite mathematical complexity that can be achieved in this effort. Also, desired information may require higher levels of space and/or time resolution than are available with any one of the currently available brain imaging techniques. This may be especially true when the desired information is about brain operations relating to consciousness. Nevertheless, there is hope that information about such brain operations will help in diagnosing and treating various detrimental conditions of consciousness, as described in Dickerson, B. C., "Advances in Functional Magnetic Resonance Imaging: Technology and Clinical Applications", *Neurotherapeutics*, Vol. 4, Issue 3, July 2007, pp. 360-370.

Unless the context indicates otherwise, the terms "circuitry" and "circuit" are used herein to refer to structures in which one or more electronic components have sufficient electrical connections to operate together or in a related manner. In some instances, an item of circuitry can include more than one circuit. An item of circuitry that includes a "processor" may sometimes be analyzed into "hardware" and "software" components; in this context, "software" refers to stored or transmitted data that controls operation of the processor or that is accessed by the processor while operating, and "hardware" refers to components that store, transmit, and operate on the data. The distinction between "software" and "hardware" is not always clearcut, however, because some components share characteristics of both; also, a given software component can often be replaced by an equivalent hardware component without significantly changing operation of circuitry.

Some implementations described below involve a "system", used herein to mean a combination of two or more parts or components, such as processors and other circuitry components, that can perform a function together. A system may be characterized by its function: for example, an "imaging system" is a system that performs imaging operations, such as on bodies or body parts; and so forth. For example, in implementations described below, imaging systems perform imaging of brains, typically based on "activity", meaning a measurable feature that correlates with activity levels in brain locations, such as blood flow, oxygen concentration, metabolic rate, and so forth.

The technique in FIG. 1 includes an operation in box 10 that obtains brain image signals, as suggested by the schematic profile of brain 12. In general, the operation in box 10 could be performed by any system or circuitry capable of obtaining brain image signals indicating activity within a brain.

An operation in box 14 uses brain image signals from the operation in box 10 to extract information from them about features of a brain's activity. The operation in box 14 can, for example, obtain values indicating information about activity features of a brain. As used herein, an "activity feature" is a feature about which information is present in activity levels of locations in a brain, and a value indicating information about an activity feature is referred to as a "feature value"; a feature value could, for example, be an identifier of an activity feature, a value indicating its presence or absence, a value indicating a measure of the feature such as its intensity, a value indicating a relationship of a feature to one or more other features, and so forth. Because of the rapid advance of brain imaging technology, it is not possible to provide a complete, up-to-date list of activity features—discoveries of new activity features are being published with increasing frequency in recent years. A few examples include understanding sarcasm, emotions such as feelings of disgust and delight, the smell of chocolate, musical hallucinations, and religious feeling.

Some implementations described below are based on the premise that a "quale" can correspond to an activity feature, where the term "quale" refers to the way it feels to have a particular simple experience, such as feeling a pain, seeing a color, smelling an odor, and so forth. In some contexts, the term "qualia", the plural of "quale", is used herein to refer collectively to the singular and to the plural, such as in the expression "one or more qualia". An activity feature that corresponds to a quale is referred to herein as a "qualia activity feature"; accordingly, a "qualia value" is a feature value that indicates information about one or more qualia activity features. Also, the brain of a living organism is referred to herein as a "living brain" and, if the organism is experiencing qualia, as a "conscious brain".

An operation in box 16 provides one or more feature values from the operation in box 14. Such an operation can be performed, for example, to make feature values available for use by a human, for performance of data processing operations that require the feature values, or, conceivably, as input data for other applications such as in process or machine control.

Boxes 20, 22, and 24 in FIG. 1 illustrate graphically an example of a technique that the operation in box 14 can perform to extract information. In addition to being "activity-based" in the sense that it depends on brain image signals that indicate activity levels, the technique in boxes 20, 22, and 24 is "region-based" in the sense that it depends on finding one or more regions that satisfy a suitable criterion. An "active region criterion", for example, is a criterion that can be used to find an active region of a brain, and some examples of active region criteria are described below in relation to implementations. Once an active region is found, it may be possible to extract information about active features within it.

More specifically, the operation in box 20 finds a set of regions of brain 12, each of which satisfies an active region criterion or other suitable criterion for region-based information extraction. Two regions in the set are illustratively labeled "A" and "B", and their shapes and sizes are suggested by isoactive contours, i.e. lines of equal activity level at a certain resolution, with line 30 being the innermost isoactive contour of region A and line 32 being the innermost isoactive contour of region B. Within each region, the innermost isoactive contour indicates the highest activity level, and the number of isoactive lines that must be crossed between each of lines 30 and 32 and the lowest level between regions A and B provides a rough measure of how the highest activity levels in the two regions are related—in the illustrated example, three lines separate line 30 from the lowest level while only two lines separate line 32 from the lowest level; therefore, the highest activity level in region A is greater than that in region B.

The operation in box 22 extracts information from a portion of the brain image signals that includes information about one of the regions found in box 20, illustratively region A. A few possible examples of activity features are shown graphically, including locations 40 and 42 at which maxima of activity occur and area 44 in which activity contrast is high. As suggested below, mathematical models can be used to extract information about these and other types of activity features that occur in active regions. As suggested by locations 40 and 42 and area 44, some techniques can extract information about highly localized activity features, while other techniques can extract information about less localized activity features. Although the illustrated technique relates to activity features that are sufficiently localized to be found within an active region, other techniques might be developed to extract information about activity features that involve more than one active region.

The operation in box 24 uses information extracted in box 22 to obtain a set of N feature values, where N is greater than zero for the illustrated example of region A. This operation can include not only obtaining values but also associating the values with activity feature identifiers. For qualia activity features, for example, a name, number, or other alphanumeric identifier of a quale could be associated with a feature value with information about the quale's corresponding qualia activity feature.

The operations in FIG. 1 could be implemented in numerous ways: For example, they could be implemented with parallel operations, with serial operations, or with any suitable combination of parallel and serial operations. Similarly, the operations could be implemented with analog signal processing, digital signal processing, or any suitable combination of analog and digital techniques. They could be implemented in a wide variety of signal processing systems.

Figure 2:
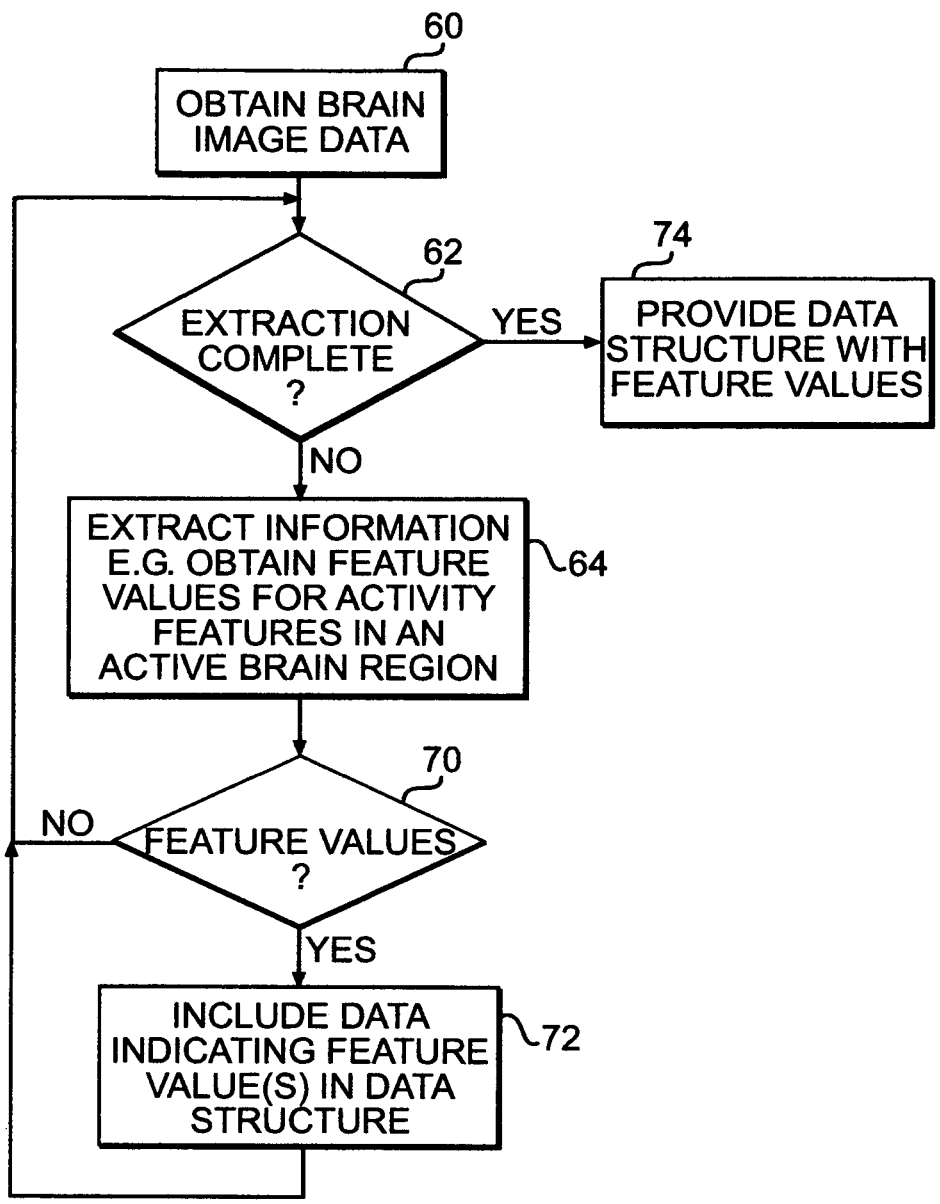
FIG. 2 is a flow chart showing general operations in a data processing implementation that provides a data structure indicating feature values for activity features of active brain regions.

FIG. 2 is a flow chart illustrating general operations that could be performed in a data processing implementation of operations in FIG. 1. Unless the context indicates otherwise, the term "data" is used herein to refer to signals in digital form, such as binary data. The term "data structure" refers to a combination of items of data that are ordered, linked, associated such as in a table, or otherwise related such that some items in the combination can be accessed based on other items; although exemplary data structures are described below as stored in memory, a data structure can take other forms, such as during transmission through a data communication network.

The operation in box 60 begins by obtaining brain image data, an implementation of the operation in box 10 in FIG. 1. The operation in box 60 can include known techniques for converting analog brain image signals into digital form in a suitable format for digital data processing. It is foreseeable, however, that additional types of brain image signals will be developed and that further techniques for converting analog brain image signals to digital form will also be developed, all within the scope of the operation in box 60.

The operation in box 62 begins an iterative loop that performs information extraction, implementing the operation in box 14 in FIG. 1. Unless a test in box 62 determines that information extraction is complete, another iteration is performed. The test could, for example, determine that sufficient information has been obtained or that a resolution limit has been reached so that further useful information cannot be obtained.

Each iteration of the loop extracts information, in box 64. As shown, one example of information extraction is to obtain one or more feature values for activity features in an active brain region, such as by implementing operations in boxes 20, 22, and 24 in FIG. 1. Each iteration can branch based on whether such features values have been obtained, as indicated in box 70. If so, the operation in box 72 can include data indicating feature values obtained in box 64 in a data structure that also includes data indicating previously obtained feature values. Other suitable operations (not shown) could be performed for other information extraction results, before returning to box 62 to begin the next iteration.

Finally, when information extraction is complete, the operation in box 74 can provide the data structure that includes feature values, implementing the operation in box 16 in FIG. 1. The data structure could, for example, be provided for human use, such as through a printed version or an interactive user interface allowing a user to see representations of feature values or in any other way a user can understand. Also, the data structure could be provided through any appropriate communication link to another system for use in further data processing operations or it could be provided by providing a link or other handle to the data structure to another process on a system that can access the data structure.

Figure 3:
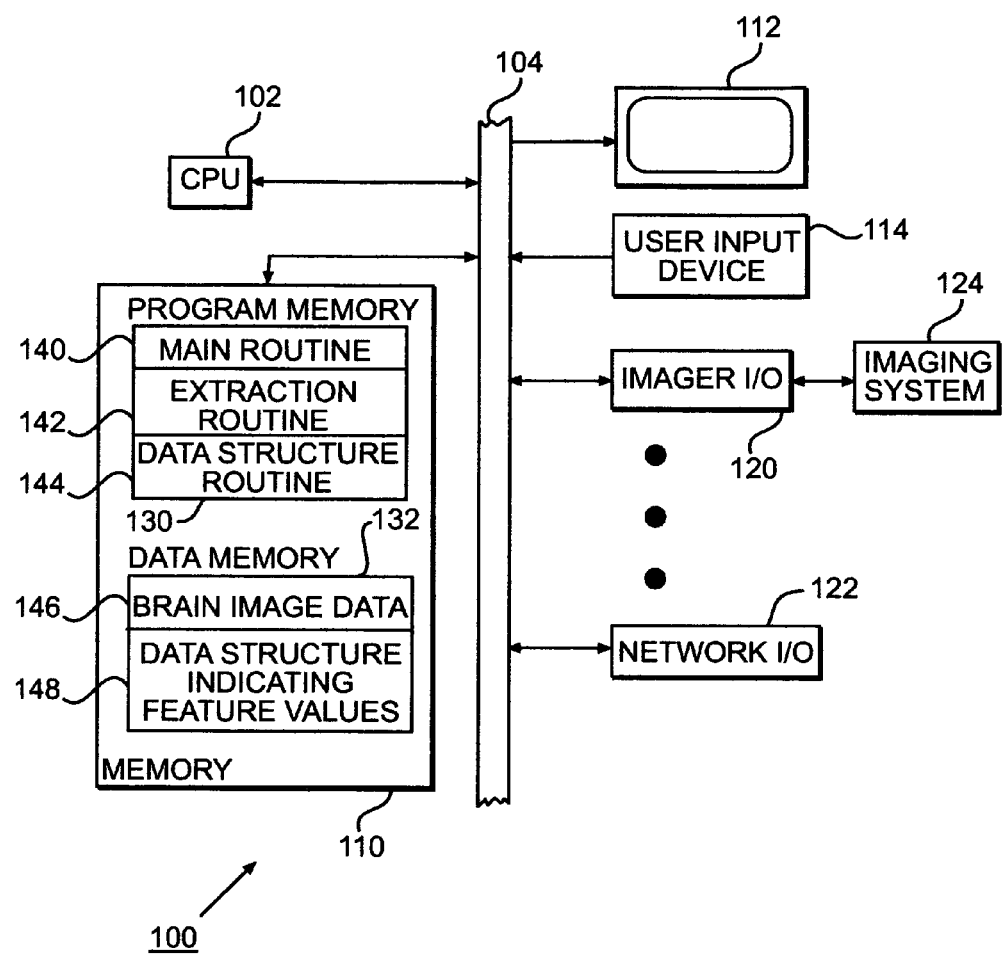
FIG. 3 is a schematic block diagram of components of a system in which operations as in FIG. 2 can be implemented.

The general data processing operations in FIG. 2 could be implemented in many ways on a variety of data processing systems. FIG. 3 illustrates general features of an implementation with a single central processing unit CPU connected to other components through a bus, but features as described herein could be implemented in many other architectures.

System 100 includes CPU 102, connected to other components through bus 104. Any suitable CPU and bus architecture could be used to implement system 100. In the illustrated example, bus 104 also connects to memory 110 as well as several input/output (I/O) devices. The I/O devices include user interface devices such as display 112 and user input device 114, which could, for example, include a keyboard and a mouse. Bus 104 could also connect to various other I/O devices, with imager I/O 120 and network I/O 122 being illustratively shown. Imager I/O 120 provides a suitable interface for exchange of signals with imaging system 124, which could perform any suitable combination of imaging techniques, e.g. PET, fMRI, EEG, MEG, and so forth. System 100 could include several imager I/O devices for exchange of signals with respective imaging systems.

Memory 110 could be implemented with any suitable combination of memory devices, including drives for storage and retrieval of information from storage media, such as magnetic or optical media. CPU 102 or another processor could perform memory management using any suitable technique. For example, in an implementation for medical purposes, such as for diagnosis or treatment of detrimental conditions of consciousness, a CD-ROM or other optical storage medium with a suitable format could store information about a given patient in a portable form that could be removed from system 100 and used in another system.

Memory 110 illustratively includes program memory 130 and data memory 132, implemented in any suitable way. In addition to various other software, program memory 130 illustratively includes main routine 140, extraction routine 142, and data structure routine 144 and data memory 132 illustratively includes brain image data 146 and data structure 148. Main routine 140 could, for example, implement the overall technique of FIG. 2, calling extraction routine 142 to perform the operation in box 64 and calling data structure routine 144 to perform data structure update in box 72 and to provide data structure 148 in box 74. The division of operations into routines and items of data is somewhat arbitrary, however, and various additional routines and subroutines could be implemented, some of which are suggested in relation to exemplary implementations described below. Also, various additional items of data could be implemented, some of which are suggested in relation to exemplary implementations described below. Further, some software components could alternatively be implemented as hardware components or with a combination of software and hardware, and some hardware components could similarly be implemented in software.

Figure 4:
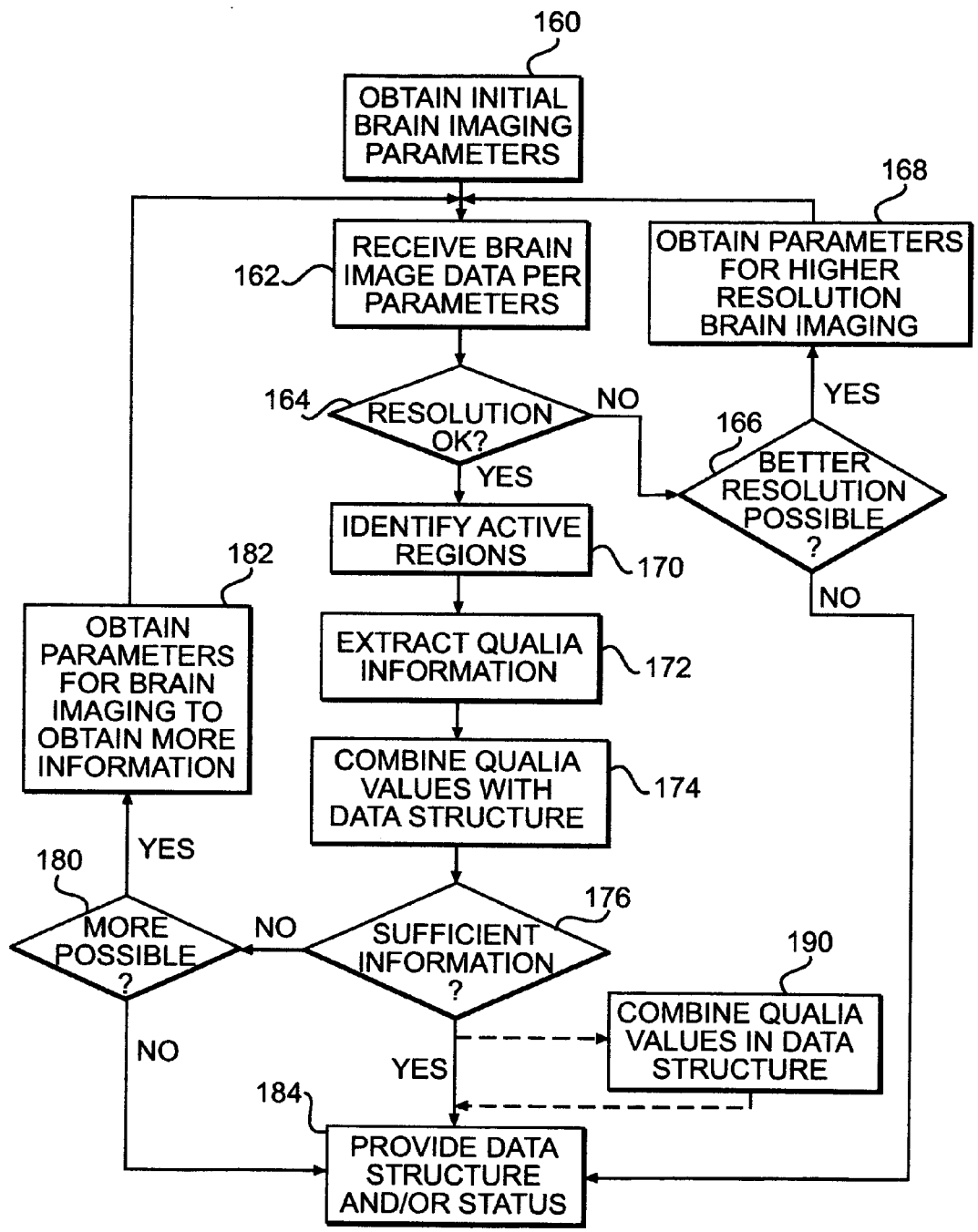
FIG. 4 is a flow chart showing a way in which a main routine could be implemented, as in the system of FIG. 3.

FIG. 4 illustrates one of many ways that main routine 140 could be implemented, illustratively to obtain a data structure indicating qualia values. In FIG. 4, main routine 140 continues to extract qualia information until either sufficient information has been obtained or a resolution limit is reached, which is one way to implement box 62 in FIG. 2.

The operation in box 160 begins by obtaining initial parameters for brain imaging. Initial parameters could be retrieved from data memory 132, could be interactively obtained through user input device 114, or could be received through network I/O 122, for example. Like other parameters described below, CPU 102 can use the initial parameters to provide signals to imaging system 124 through imager I/O 120 to obtain a desired type of brain image data. Imaging system 124 may have its own operator interface, and an alternative approach would be for an operator of imaging system 124 to provide initial parameters and take other steps needed for system 124 to obtain a desired type of brain image data which it would then provide to system 100 through imager I/O 120.

As a result of operation of system 124 in accordance with parameters from box 160 or elsewhere as described below, the operation in box 162 receives brain image data from system 124. The operation in box 162 can also include storing brain image data 146 in data memory 132, which is useful in the usual case in which brain image data cannot be adequately processed in real time. The operation in box 164 can then perform an initial evaluation of brain image data received in box 162 to determine whether it provides information with sufficient resolution for information extraction, which could require some minimum space and/or time resolution. The operation in box 164 could also be implemented to detect malfunctions or other problems with operation of system 124 that result in inadequate resolution.

If resolution is not adequate, the operation in box 166 determines whether better resolution is possible, such as by operating system 124 (or another imaging system, not shown) with different parameters or by again operating system 124 with the same parameters but without malfunction or other problems that occurred. If so, the operation in box 168 obtains parameters for higher resolution brain imaging, and brain image data is again received in box 162.

When brain image data 146 has adequate resolution, the operation in box 170 can use brain image data 146 to identify active brain regions, and the operation in box 172 can then extract qualia information for the active brain regions identified in box 170. The qualia information can include qualia values, and the operation in box 174 can combine the qualia values with a data structure that includes previously obtained qualia values. Although shown as a sequence of separate boxes, the operations in boxes 170, 172, and 174 can be implemented in numerous ways, in some of which they do not occur entirely in sequence.

The operation in box 176 determines whether sufficient information has been obtained. For example, if the information will be used in diagnosis or treatment of a detrimental condition of consciousness, the operation in box 176 could include an interactive test allowing a doctor or other user to determine and indicate whether the information is sufficient. It may also be possible to implement an automated sufficiency criterion, allowing an automatic determination whether the information is sufficient. If not, the operation in box 180 determines whether it is possible to obtain more information by further brain imaging; this operation could also be performed interactively or automatically. If more information is possible, the operation in box 182 obtains parameters for further brain imaging to obtain more information, in a manner similar to box 168, as described above, and brain image data is again received in box 162. It would be possible for the further brain imaging to be performed with a different modality that provides additional information, such as because it has different resolution characteristics. In a coarse/fine approach, one modality, e.g. fMRI, could be used initially to identify active brain regions in box 170, then another, e.g. MEG, could be used to extract qualia information in box 172.

When sufficient information has been obtained, or if better resolution and more information are both impossible, the operation in box 184 provides the data structure indicating qualia values and/or provides status information. Status information could, for example, include one or more error messages or other explanation of results. As suggested by the dashed lines to box 190, another optional step before providing the data structure is to further combine qualia values in the data structure. This could be desirable where the operation in box 174 leads to a suboptimal data structure that can be improved by the operation in box 184, such as to make it more compact. It would even be possible for box 174 to simply concatenate qualia values somehow, and for the operation in box 190 to then make the data structure optimal in other ways, such as to permit rapid access to a desired qualia value.

Figure 5:
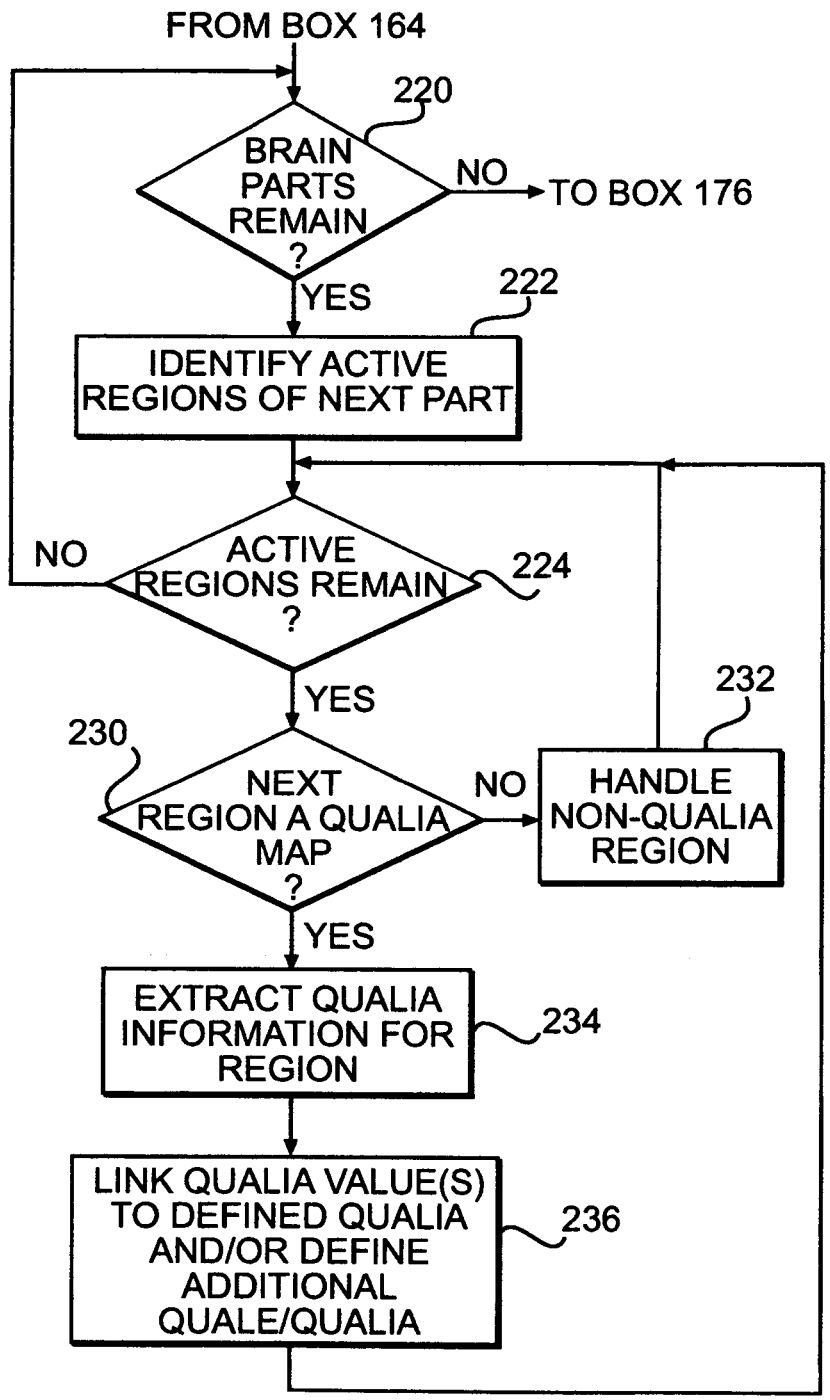
FIG. 5 is a flow chart showing an exemplary implementation of certain operations that could be included in a technique as in FIG. 4.
Figure 6:
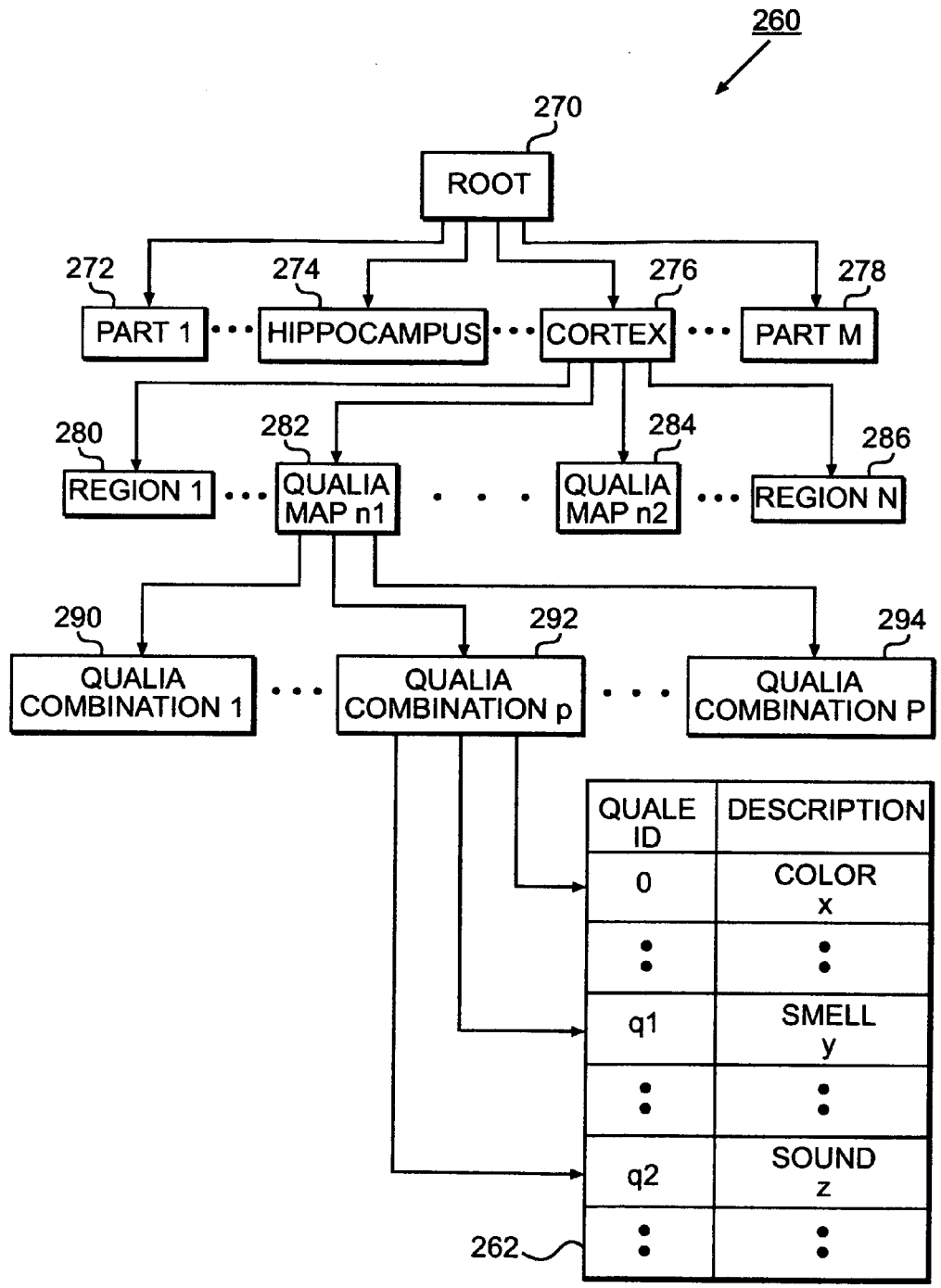
FIG. 6 is a schematic diagram showing features of a data structure that can be used in an implementation as in FIG. 5.
Figure 7:
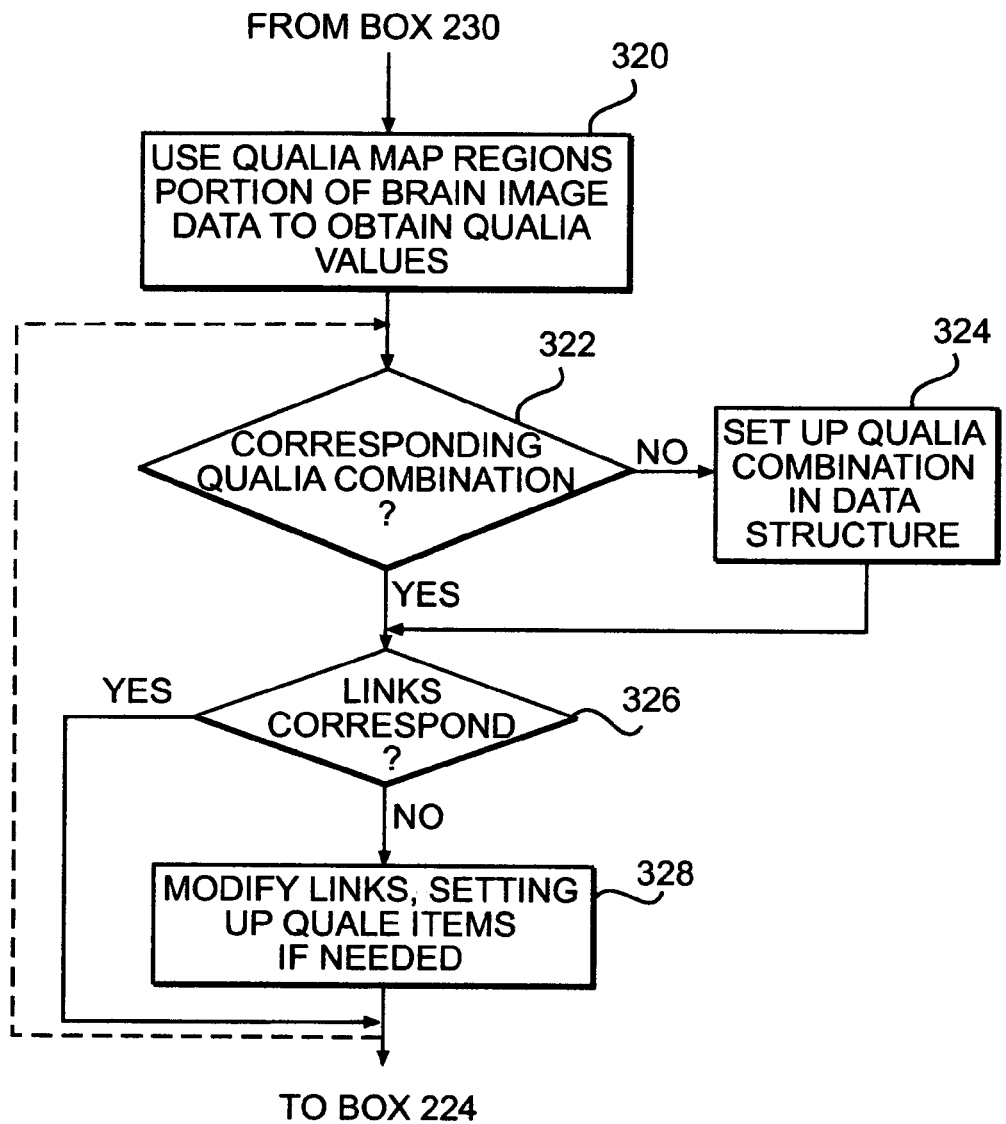
FIG. 7 is a flow chart showing an exemplary implementation of certain operations that could be included in a technique as in FIG. 5.

FIGS. 5-7 illustrate in greater detail features of an exemplary implementation that could be used for boxes 170, 172, and 174 in FIG. 4. FIG. 5 shows an overall flow chart, FIG. 6 features of a data structure, and FIG. 7 a detailed flow chart.

In FIG. 5, the operation in box 220 begins an outer, part-level iterative loop after the operation in box 164 determines that resolution of brain image data 146 is adequate. Each outer iteration uses a portion of brain image data 146 with information about a respective brain part, e.g. in a human brain, a hemisphere or other part of the cerebral cortex, the hippocampus or other part of the limbic system, the cerebellum, etc. The outer iterative loop identifies active regions of the next brain part, in box 222, and then the operation in box 224 begins an inner, region-level iterative loop, each iteration of which uses a portion of brain image data 146 with information about a respective one of the active regions from box 222. The operation in box 222 could be implemented by comparing activity levels at positions or groups of positions in the brain part with an appropriate threshold activity level. Different thresholds could be appropriate for different parts or even for different positions within a part or to differently sized groups of positions. Rather than thresholds, contrasts could be used; for example, an active region criterion could require that the region have at least a certain contrast in relation to neighboring activity level minima on all sides or on a certain number of sides. Because parts of the brain generally have complex shapes, a brain part's activity pattern could also, for example, be projected onto a suitable surface such as a plane before applying an active region criterion such as a threshold-based or contrast-based criterion. Various other active region criteria could be developed.

Each inner iteration branches based on whether the next active region is a qualia map. The term "map" is used herein to refer broadly to a brain part that can respond to neural inputs with one of two or more activity level patterns. Some relatively complex maps are described in Blakeslee, S. and Blakeslee, M., *The Body has a Mind of Its Own—How Body Maps in Your Brain Help You Do (Almost) Everything Better*, New York: Random House, 2007, but the term "map" is used herein to include, in addition to complex maps, even very simple maps that have only two activity level patterns, analogous to ON and OFF. A "qualia map", then, is a map that has at least one activity level pattern that corresponds to a quale. In the implementation of FIG. 5, the determination whether a region is a qualia map can be based on previously confirmed qualia map regions or, as appropriate, can be interactively or automatically determined in another appropriate way, such as through input from a human expert.

If the region is not a qualia map, the operation in box 232 can handle it in a way appropriate for non-qualia regions. Information about non-qualia regions can be useful for many different purposes, and could also be included in a data structure that indicates qualia values.

If the region is a qualia map, the operation in box 234 can extract qualia information for the region from the relevant portion of brain image data 146. The extracted qualia information can include, for example, qualia values for one or more qualia that correspond to activity level patterns of the region. Up to this point, the operations in FIG. 5 can be seen to be an implementation of extraction routine 142 (FIG. 3), and the operation in box 234 completes extraction operations for a given region.

After qualia values are obtained in box 234, the operation in box 236 can include the qualia values in the data structure with previously obtained values. If a set of one or more qualia values corresponds to a quale that has already been defined in the data structure, the operation in box 236 can link the qualia values to that quale; otherwise, an additional quale or additional qualia can be defined in the data structure, and qualia values can be linked to the additional quale/qualia. The operation in box 236 can thus include qualia values from box 234 in the data structure, and can therefore be seen as an implementation of data structure routine 144 (FIG. 3).

Inner iterations are performed until the operation in box 224 determines that all active regions of the current brain part have been handled. Similarly, outer iterations are performed until the operation in box 220 determines that all brain parts have been handled. If so, the operation in box 220 branches to box 176, to test whether sufficient information has been obtained.

FIG. 6 shows data structure 260, which includes a part illustrated as a node-link structure and a part illustrated as table 262. Table 262 illustratively holds items that are pairs, with each pair including a quale identifier and a descriptor of the corresponding quale. In order to add a new quale, an item for the quale can be added to table 262, including a quale ID and a descriptor. In the illustrated example, quale IDs 0, q1, and q2 have been assigned respectively to color x, smell y, and sound z.

The node link structure has four levels, with root 270 being the only node at the root level, and linked to M nodes at the brain part level, including nodes 272, 274, 276, and 278. Node 274 illustratively represents the hippocampus, while node 276 illustratively represents the cerebral cortex.

Each node at the brain part level can be linked to one or more nodes at the region level, with node 276 for the cortex illustratively linked to N region nodes, including nodes 280, 282, 284, and 286. Nodes 282 and 284 are illustratively qualia map regions, labeled qualia map n1 and qualia map n2.

Nodes at the region level that represent qualia map regions can in turn be linked to one or more nodes at the qualia combination level. Node 282 for qualia map n1 is illustratively linked to P qualia combination nodes, including nodes 290, 292, and 294.

Nodes at the qualia combination level can be linked to items in table 262 for quale that are included in the corresponding qualia combination. Node 292 for qualia combination p is linked to the items with quale IDs 0, q1, and q2 as described above, and therefore corresponds to a qualia combination that includes color x, smell y, and sound z. Note that more than one qualia combination can link to a given item in table 262.

As can be seen, the basic framework of data structure 260 might be the same for many conscious brains, with specific details being different and with the particular regions that are active qualia map regions and with their specific qualia combinations both changing over time. Therefore, data structure 260 may be implemented as a partially completed data structure, with operations in FIG. 5 filling in additional parts.

Data structure 260 could be implemented in a wide variety of ways. For example, each node could be encoded as an item of data including information about the brain part or qualia combination it represents, while links between nodes could be pointers to nodes. Table 262 could be implemented as a sequence of descriptors, with each descriptor's position in the sequence corresponding to its quale ID. Many other ways of implementing such a data structure are available.

FIG. 7 shows in greater detail one way in which boxes 234 and 236 in FIG. 5 could be implemented for data structure 260 in FIG. 6. As indicated below, the technique of FIG. 7 can extract information about qualia based on a mathematical model of consciousness.

As shown, the operation in box 320 can follow a determination in box 230 (FIG. 5) that an active region of a brain part is a qualia map. The operation in box 320 uses the qualia map region's portion of brain image data 146 to obtain qualia values. Although this operation could be implemented in many ways, a mathematical model of consciousness may provide a useful starting point.

One type of model, referred to herein as "neural clique models", relates to Tsien, J. Z., "The Memory Code", *Scientific American*, July 2007, pp. 52-59, which describes how small groups of neurons in the hippocampus perform as a unit. An exemplary equation for a neural clique model of consciousness can be expressed as follows:

$$\text{Quale } M(T) = (\text{ON iff Activity(Neural Clique } M, T) > \text{Threshold } M; \text{else OFF})$$

In words, this means that the respective Quale M for Neural Clique M will be ON (i.e. consciously experienced) at time T if and only if an Activity level of Neural Clique M at time T is greater than the value of its respective Threshold M; when the Activity level does not exceed the value of Threshold M, Quale M will be OFF. An operation in box 320 could apply this equation by applying suitable thresholds to activity levels at brain positions that are within a qualia map region and whose activity levels correspond with qualia. The combination of resulting values, such as a vector or other data item, is an example of a qualia value that could be included in a data structure as described herein.

Another type of model, referred to herein as "conscious cavity models", was proposed by Beran, J. T., "Disambiguation in Conscious Cavities", *Quantum Mind 2007 Conference Abstracts*, Salzburg, Austria, July 2007, p. 30. A conscious cavity can be thought of as a neural structure that can produce any of a set of conscious experiences. Structures that might operate as conscious cavities could occur, for example, in the cerebral cortex and in the limbic system in brains of humans and in similar brains. The following inner product equation has been proposed for conscious cavity models:

$$<\text{Qualia } N(T)|\text{Neural Input}(Cavity, T)> = \text{Activity}(Cavity, T)$$

In words, this means that a projection of a Cavity's Neural Input vector onto Qualia N (a vector for one of the conscious experiences the Cavity can produce) at time T is equal to an Activity value of the Cavity at time T, where the Activity value is, e.g., a real or complex scalar. For a purely probabilistic case, for example, the probability of Qualia N in response to a given Neural Input to the Cavity could be equal to a suitably normalized (between zero and one) Activity value for the Cavity, which could be expressed as follows:

$$Pr(\text{Qualia } N(T)|\text{Neural Input}(Cavity, T)) = \text{Activity}(Cavity, T)$$

As can be seen, this equation yields the same result as the above neural clique equation if Activity has a transition at Threshold between two of Cavity's possible qualia, one with Quale M ON (i.e. Probability=1) and the other with Quale M OFF, (i.e. Probability=0).

The conscious cavity inner product equation is therefore consistent with thresholding, but also is consistent with other ways of obtaining qualia values, such as by taking multiple activity level measurements to obtain probabilities or by analyzing time varying activity levels that can be analyzed into frequency spectra, and so forth. The inner product equation is very robust, and it probably can be simplified in many other ways with suitable simplifying assumptions to develop additional techniques for extracting qualia values.

The operation in box 322 tests whether the values obtained in box 320 correspond to an existing qualia combination node in data structure 260. For this purpose, each qualia combination node can have a respective criterion for determining whether a set of values correspond to it. If there is no corresponding existing node, the operation in box 324 sets up a new qualia combination node linked to the current qualia map region.

In either case, the operation in box 326 tests whether the qualia values from box 320 completely match the links to table 262 from the qualia combination node. If not, appropriate modifications in the links can be made. For example, if a qualia combination node does not link to a quale that is defined in table 262 but the qualia values indicate presence of that quale, an additional link can be added from the qualia combination node to the quale's item in table 262, provided this would not result in violations of the qualia combination's criterion for determining whether values correspond to it. Or, if the qualia combination node is newly added, new links must be created to existing quale items in table 262; also, new quale items must also be set up in table 262 for any qualia in the combination that are not already defined, and then new links to the new quale items must be added. For some such situations, table 262 could contain a default quale item that can always be automatically linked to in default of an existing quale item in table 262; at a later time, interactive operations could be performed to define new quale items to which links can be made rather than to the default quale item.

When links have been modified in box 328 or when box 326 determines that all links correspond, it would be possible to again perform the operation in box 322 if additional qualia combinations correspond to qualia values from box 320, but, as suggested by the dashed line back to box 322, this is not expected to be a typical case. More typically, the operation in box 224 (FIG. 5) can again be performed to begin the next inner iteration.

Techniques as described above offer the possibility of more effectively extracting information about activity features of brain regions, especially of qualia map regions. The resulting information could assist in diagnosis and/or treatment of detrimental conditions of consciousness. It could be included in data structures that can be stored on a suitable storage medium for convenient access and transfer.

While the invention has been described in conjunction with specific exemplary implementations, it is evident to those skilled in the art that many alternatives, modifications, and variations will be apparent in light of the foregoing description. Accordingly, the invention is intended to embrace all other such alternatives, modifications, and variations that fall within the spirit and scope of the claims now or hereafter appended.

The invention claimed is:

1. A method of operating a system having:
   a processor,
   receiving circuitry that, in operation, receives brain image signals indicating activity at locations in brains, and
   memory circuitry that, in operation, stores:
      program data indicating a program, and
      a data structure,
   the method comprising:
      operating the receiving circuitry to obtain brain image signals indicating activity at locations in a conscious human's brain; the brain image signals including electrical/magnetic signals obtained using at least one of positron emission tomography, functional magnetic resonance imaging, electroencephalography, and magnetoencephalography;
      operating the processor to perform the program; in performing the program, the processor extracting information from the brain image signals and including at least part of the extracted information in the data structure; and
      using the data structure in at least one of:
         diagnosis of a detrimental condition of consciousness; and
         treatment of a detrimental condition of consciousness;
   the act of operating the processor including:
      for each of a set of two or more brain parts, performing a respective part level iteration;
   each part's respective part level iteration including:
      obtaining region identifying data indicating regions of the brain part; and
      for each of a set of the regions indicated by the part's region identifying data, performing a respective region level iteration that obtains feature values indicating activity features of the region;
   the respective region level iteration of one or more regions including:
      obtaining respective qualia information based on a portion of the brain image signals that indicates activity levels of locations in the region; at least one region's qualia information including, for each quale activity feature in a set of one or more activity features that can occur in the region, a respective qualia value indicating the human's current experience corresponding to the quale activity feature; and
      including in the data structure qualia value data indicating, for at least one quale activity feature that can occur in one of the set of regions, the respective qualia value.

2. The method of claim 1 in which the act of performing a respective region level iteration includes at least one of:
   applying a threshold to activity levels at positions within the region;
   obtaining probabilities for activity levels at positions within the region; and
   obtaining frequencies from time varying activity levels at positions within the region.

3. The method of claim 1 in which at least one of the set of qualia activity features includes a respective combination of two or more qualia; the act of including qualia value data in the data structure further including in the data structure:
   for one of the respective combinations of two or more qualia, a qualia combination node corresponding to the combination; and
   linked to the qualia combination node, a respective item for each of the qualia in the combination, at least one respective item including a descriptor of the respective one of the qualia in the combination.

4. A system comprising:
   a storage medium;
   stored by the storage medium, a data structure;
   a processing component that includes one or more processors; and
   connecting circuitry that can receive brain image data indicating activity at locations in a living brain and through which the processing component can access the data structure stored by the storage medium;
   the data structure including:
      for each of a set of regions of a living brain, qualia feature value data indicating, for each of a set of one or more qualia activity features the region can have, a respective qualia value, the qualia value indicating a conscious experience of the brain corresponding to the qualia activity feature; at least one of the set of qualia activity features including a respective combination of two or more qualia;
      a node-link structure that includes:
         a qualia combination node corresponding to one of the respective combinations of two or more qualia; and a region node that represents an active qualia map region of the living brain, the region node being linked to the qualia combination node; and linked to the qualia combination node, a respective item for each of the qualia in the combination, at least one respective item including a descriptor of the respective one of the qualia in the combination;

the processing component including a combination of one or more processors programmed:

to use the brain image data to obtain feature value data indicating feature values of active regions of the living brain; the feature value data for the active qualia map region including, for a quale activity feature that can occur in the active qualia map region, a value indicating the living brain's current experience corresponding to the quale activity feature; and to include in the data structure the value indicating the living brain's current experience corresponding to the quale activity feature.

5. The system of claim 4 in which the combination of one or more processors includes only one programmed processor.

6. The system of claim 4, further comprising an imaging system that provides the brain image data to the connecting circuitry; the imaging system obtaining the brain image data by at least one of positron emission tomography, functional magnetic resonance imaging, electroencephalography, and magnetoencephalography.

7. The system of claim 4 in which the combination of two or more qualia includes at least one of a color, a smell, and a sound.

8. The system of claim 4 in which the data structure further includes a table, the table including:

for each of the qualia in the combination, the respective item.

9. A method of operating the system of claim 4, comprising:

operating the combination of one or more processors as programmed; the act of operating the combination of one or more processors as programmed comprising:

performing a respective part level iteration for each of a set of two or more brain parts; each part's respective part level iteration obtaining region identifying data indicating regions of the brain part; the active qualia map region being one of the regions indicated by the region identifying data of one of the brain parts in the set; the node-link structure including a respective brain part node that represents the one of the brain parts, the respective brain part node being linked to the region node that represents the active qualia map region; and for each of a set of the regions indicated by the part's region identifying data, performing a respective region level iteration that obtains feature values indicating activity features of the region;

the respective region level iteration of the active qualia map region obtaining respective qualia information based on a portion of the brain image signals that indicates activity levels of locations in the active qualia map region; the respective qualia information including, for each quale activity feature in a set of one or more activity features that can occur in the active qualia map region, a respective qualia value; the value indicating the living brain's current experience being the respective qualia value of one of the quale activity features in the set of activity features that can occur in the active qualia map region.

10. The method of claim 9 in which the brain is a conscious human's brain.

11. A method of operating the system of claim 4, comprising:

using the active qualia map region's portion of brain image data to obtain a set of qualia values based on a mathematical model of consciousness; and determining whether the data structure includes an existing node corresponding to the set of qualia values by testing whether the qualia values in the set correspond to the qualia combination node.

12. A method of operating the system of claim 4, the method comprising:

operating the connecting circuitry to receive brain image data indicating activity at locations in the living brain;

operating the combination of one or more processors to extract information from the brain image data; the act of operating the combination of one or more processors to extract information including:

obtaining one or more respective feature values indicating activity features of the active qualia map region.

13. The method of claim 12 in which the act of obtaining feature values includes:

obtaining active region data that indicate the active regions; and for each of the active regions indicated by the active region data, performing a respective iteration, each active region's iteration including:

obtaining the active region's feature values.

14. The method of claim 13 which the active region data indicate two or more active regions, the respective iterations of the active regions being performed in a series; after each preceding iteration in the series, a respective following iteration combining the feature values it obtains with a combined feature value data structure from the preceding iteration.

\* \* \* \* \*